(12) United States Patent
Pardonge et al.

(10) Patent No.: US 8,136,519 B2
(45) Date of Patent: Mar. 20, 2012

(54) DEVICE FOR DISPENSING A FLUID PRODUCT

(75) Inventors: Jean-Marc Pardonge, Les Authieux sur Port Saint Ouen (FR); Salim Haffar, L'étang la Ville (FR)

(73) Assignee: Valois S.A.S., Le Neubourg (FR)

( * ) Notice: Subject to any disclaimer, the term of this patent is extended or adjusted under 35 U.S.C. 154(b) by 1222 days.

(21) Appl. No.: 11/792,409

(22) PCT Filed: Dec. 13, 2005

(86) PCT No.: PCT/FR2005/051078
§ 371 (c)(1),
(2), (4) Date: Jul. 23, 2007

(87) PCT Pub. No.: WO2006/064159
PCT Pub. Date: Jun. 22, 2006

(65) Prior Publication Data
US 2008/0017188 A1    Jan. 24, 2008

(30) Foreign Application Priority Data
Dec. 17, 2004 (FR) .................................. 04 53057

(51) Int. Cl.
*A61M 11/00* (2006.01)
(52) U.S. Cl. .......... 128/200.14; 128/200.19; 128/200.23
(58) Field of Classification Search ............. 128/200.14, 128/200.19, 200.23, 203.12
See application file for complete search history.

(56) References Cited

U.S. PATENT DOCUMENTS

| | | | | |
|---|---|---|---|---|
| 4,291,688 A * | 9/1981 | Kistler | ...................... | 128/200.23 |
| 5,284,133 A * | 2/1994 | Burns et al. | ............... | 128/200.23 |
| 5,664,557 A | 9/1997 | Makiej, Jr. et al. | | |
| 6,305,371 B1 | 10/2001 | Frid et al. | | |
| 6,615,827 B2 * | 9/2003 | Greenwood et al. | ...... | 128/200.23 |
| 7,275,660 B2 | 10/2007 | Stradella et al. | | |
| 7,819,116 B2 * | 10/2010 | Brand et al. | ............. | 128/200.23 |
| 2003/0183226 A1 | 10/2003 | Brand et al. | | |
| 2004/0089292 A1 | 5/2004 | Pollet et al. | | |
| 2006/0163275 A1 | 7/2006 | Stradella et al. | | |

FOREIGN PATENT DOCUMENTS

| | | |
|---|---|---|
| CN | 2568777 Y | 8/2003 |
| EP | 1 304 086 A2 | 4/2003 |
| EP | 1 475 116 A2 | 11/2004 |
| WO | WO 92/17231 A1 | 10/1992 |

(Continued)

OTHER PUBLICATIONS

Chinese Office Action for CN 200580042895.4, dated Oct. 10, 2008.

(Continued)

*Primary Examiner* — Steven Douglas
(74) *Attorney, Agent, or Firm* — Sughrue Mion, PLLC

(57) ABSTRACT

A fluid dispenser device comprising: a reservoir (1) of fluid to be dispensed; a dispenser member (2), such as a pump or a valve, mounted on said reservoir (1); and a body (3) that is suitable for receiving said reservoir (1), said body (3) being provided with a dispenser orifice and an opening (310) through which said reservoir (1) can be inserted into the body (3), said reservoir (1) being displaceable in said body (3) between a rest position and a dispensing position, said reservoir (1) being removable from said body (3); said reservoir (1) and said body (3) including respective ID means (10, 11) that make it possible to associate said reservoir (1) with said body (3).

10 Claims, 1 Drawing Sheet

FOREIGN PATENT DOCUMENTS

| | | |
|---|---|---|
| WO | WO 00/16836 A1 | 3/2000 |
| WO | WO 02/092152 A1 | 11/2002 |
| WO | 2004/013582 A1 | 2/2004 |
| WO | WO2004/041334 * | 5/2004 |

OTHER PUBLICATIONS

Chinese Notification of Reexamination for CN 200580042895.4, dated Apr. 25, 2011.

* cited by examiner

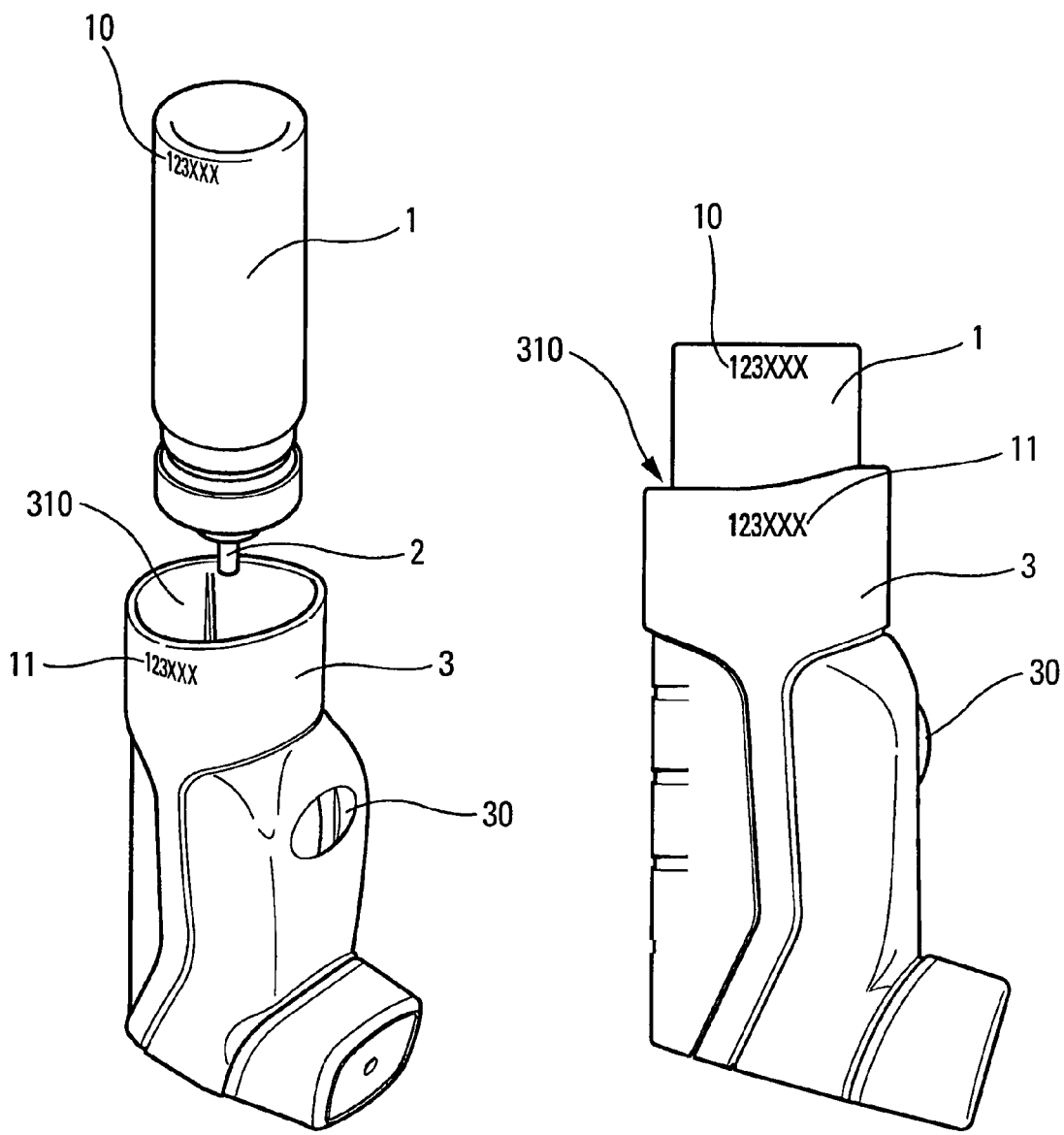

DEVICE FOR DISPENSING A FLUID PRODUCT

The present invention relates to a fluid dispenser device.

Advantageous fields of application of such a device are particularly, but not exclusively, the fields of pharmacy, cosmetics, and perfumery.

Dispenser devices of the prior art generally comprise a fluid reservoir on which there is mounted a dispenser member such as a pump or a valve. The dispenser member generally comprises a metering chamber in which an actuator rod or a valve member is slidably mounted. In particular for aerosol devices in which the fluid is expelled by means of a propellant gas through a metering valve, the reservoir is generally slidably mounted in the body so as to actuate the valve member. Connecting the body to the valve member mounted on the reservoir defines a working position of the device in which said valve member co-operates with the body. In the working position, the valve member is thus displaceable between a rest position and a dispensing position following actuation by the user. Generally, it is necessary, after several actuations of the valve member, to clean the interface between the valve member and the body. Residue of dispensed fluid may be deposited on the walls of the connection sleeve cooperating with the valve member. Unfortunately, the residue is capable of polluting the fluid that remains to be dispensed from the reservoir, indeed it is even capable of hindering the expulsion of the fluid. For such cleaning, the user must thus disengage the valve member from the connection sleeve and remove the reservoir from the body. Such disengagement thus results in a withdrawn position of the device in which the valve member does not co-operate with the body. The body and the reservoir are thus likely to be mislaid, or, following a cleaning operation, there is even a risk of swapping over bodies and reservoirs belonging to different users. Such a situation can occur in particular in hospital care services in which large numbers of dispenser devices are cleaned. Thus, if two reservoirs are swapped over, there exist possible risks of problems of hygiene and in particular microbiological contamination for the user, in particular when the dispenser device is a dispenser device using a mouthpiece. In addition, if reservoirs that do not carry information regarding the identity of the fluid that they contain are mixed up, then the user of a pharmaceutical might absorb or inhale a wrong fluid, e.g. having allergic effects or effects that are likely to generate incompatibilities between medicines. Swapping over two reservoirs after cleaning is particularly dangerous when the device is provided with a dose counter or indicator, in particular when the counter is secured to the body. A reservoir mix up could have dramatic consequences if the user ends up with a counter displaying a number of doses for dispensing that is greater than the number of doses actually remaining in the reservoir. The user thus risks ending up with an empty reservoir, while the counter indicates that doses remain to be dispensed. The risk to health is thus very significant.

Documents WO 32/17231 and US 2003/183226 disclose very complex and costly electronic systems that make it possible to associate a reservoir with an inhaler.

An object of the present invention is to provide a dispenser device that does not have the above-mentioned drawbacks.

In particular, an object of the present invention is to provide a fluid dispenser device that avoids the risk of accidentally swapping over the reservoir, in particular after cleaning the device.

More particularly, an object of the present invention is to provide a dispenser device that is simple and inexpensive to manufacture and to assemble.

The present invention thus provides a fluid dispenser device comprising: a reservoir of fluid to be dispensed; a dispenser member, such as a pump or a valve, mounted on said reservoir; and a body that is suitable for receiving said reservoir, said body being provided with a dispenser orifice and an opening through which said reservoir can be inserted into the body, said reservoir being displaceable in said body between a rest position and a dispensing position, said reservoir being removable from said body; said reservoir and said body including respective identification (ID) means that make it possible to associate said reservoir with said body.

Advantageously, the ID means of the reservoir are identical to the ID means of the body. Thus, a single reservoir and a single body include the same marking, such that the user avoids accidentally swapping over the reservoirs after cleaning the body, when the reservoir is put back in place in the body.

Advantageously, said ID means are visual and/or tactile.

Advantageously, said ID means include markings, in particular made by etching and/or printing.

Advantageously, a single reservoir includes ID means that are associated with the ID means of a specific body.

Advantageously, said body is provided with a counter or indicator device for counting or indicating the doses of fluid that have been dispensed or that remain to be dispensed from the reservoir.

In an advantageous characteristic of the invention, said counter or indicator device is actuated by displacing the reservoir between its rest and dispensing positions.

Advantageously, said ID means do not have electronic means.

Other characteristics and advantages of the present invention appear more clearly from the following detailed description of an embodiment of the invention, given by way of non-limiting example, and with reference to the accompanying drawings, in which:

FIG. 1 is a diagrammatic perspective view of a dispenser device of the invention with the reservoir separate from the body; and FIG. 2 is a diagrammatic side view of the FIG. 1 dispenser device with the reservoir inserted in the body.

The dispenser device of the present invention advantageously comprises a reservoir 1, a dispenser member 2, and a body 3, the reservoir 1 being assembled in removable manner in said body 3.

The reservoir 1 can present any appropriate shape. In particular, the reservoir can include a generally circular cylinder containing fluid at atmospheric pressure or fluid under pressure.

The dispenser member 2 can be a pump or a valve, preferably a metering valve, the operation of which is not described in greater detail. For a valve, generally used with devices of the aerosol type, a valve member is used that is displaceable in a metering chamber so as to expel the dose of fluid by means of a propellant gas. The reservoir 1 is mounted to slide axially in said body. This axial displacement causes the valve member to be displaced, and thus causes the valve to be actuated, thereby making it possible to empty said metering chamber.

In the embodiment shown in the various Figures, the body 3 is a typical body for an inhaler. The body can comprise a substantially cylindrical shell including a top end defining an opening 310 for receiving the reservoir 1. It should be observed that the body as shown is only one embodiment. Bodies of any other configuration could very well be envisaged such as the bodies that are conventionally used for nasal or otological (ear) applications, or even in the field of perfumery or cosmetics.

The reservoir 1 is inserted in the body 3 via the opening 310. Then, the reservoir 1 is assembled in the body 3 by fitting the valve member into a connection sleeve (not shown). In the present embodiment, the dispenser device shown can be actuated in conventional manner by pressing on the bottom of the reservoir 1. In use, the valve co-operates with the body 3 between a rest position and a dispensing position.

In the invention, ID means 10, 11 are provided on the reservoir 1 and the body 3 respectively, so as to associate always the same reservoir with the same body, e.g. after cleaning, requiring the reservoir to be removed from the body. The ID means on the reservoir and on the body are preferably identical and unique, i.e. the same marking appears only on a single reservoir associated with a single body. For example, it is possible to envisage a number, a symbol, or any other appropriate means. The ID means can be visual or tactile, e.g. in braille for blind people. Advantageously, as shown in the drawings, the ID means are disposed in the proximity of each other when the reservoir is in the assembled position, so as to alert the user visually in the event of error.

The ID means can be made by etching or printing, for example. In a variant, it is possible to envisage using appropriate labels. Other variants can also be envisaged, such as silk-screen printing. The ID means are advantageously applied to the device at the factory when the reservoir is assembled in the body.

A particular advantage of the invention is to be able to associate a reservoir with a body in very simple and inexpensive manner. In particular, the ID means of the invention do not have electronic means or the like.

In a particularly advantageous embodiment, the body 3 can be provided with a counter or indicator device 30 for counting or indicating the doses of fluid that have been dispensed or that remain to be dispensed from the reservoir 1. As shown, the counter can form part of said body 3. The counter or indicator device can be actuated by displacing the reservoir between its rest and dispensing positions. As a result of the presence of the ID means 10, 11, the user or the cleaner does not risk accidentally swapping over the reservoirs after cleaning. Consequently, the same reservoir 1 is always associated with its respective body 3, and the number of doses that are indicated by the counter 30 of the body necessarily corresponds to the correct number of doses that have been dispensed or that remain to be dispensed from the reservoir 1.

Although the present invention is described above with reference to a particular embodiment thereof, it is clear that it is not limited by said embodiment. On the contrary, any useful modification can be applied thereto by the person skilled in the art, without going beyond the ambit of the present invention, as defined by the accompanying claims.

The invention claimed is:

1. A fluid dispenser device comprising:
    a reservoir (1) of fluid to be dispensed;
    a dispenser member (2) mounted on said reservoir (1); and
    a body (3) that is suitable for receiving said reservoir (1), said body (3) being provided with a dispenser orifice and an opening (310) through which said reservoir (1) can be inserted into the body (3), said reservoir (1) being displaceable in said body (3) between a rest position and a dispensing position, said reservoir (1) being removable from said body (3);
    said reservoir (1) and said body (3) include respective ID means (10, 11) that make it possible to uniquely associate said reservoir (1) with said body (3), the ID means (10) of the reservoir (1) being uniquely associated with the ID means (11) of the body (3), thereby preventing another reservoir from being accidentally associated with the body;
    said body is provided with a counter or indicator device for counting or indicating doses of fluid that have been dispensed or that remain to be dispensed from the reservoir.

2. A device according to claim 1, in which said ID means (10, 11) are visual and/or tactile.

3. A device according to claim 1 in which said ID means (10, 11) include markings, in particular made by etching and/or printing.

4. A device according to claim 1, in which a single reservoir (1) includes ID means (10) that are associated with the ID means (11) of a specific body (3).

5. A dispenser device according to claim 1, in which said counter or indicator device (30) is actuated by displacing the reservoir (1) in the body (3) between its rest and dispensing positions.

6. A device according to claim 1, in which said ID means (10, 11) do not have electronic components.

7. The dispenser device according to claim 1, wherein the dispenser member is a pump or a valve.

8. A fluid dispenser device comprising:
    a reservoir of fluid to be dispensed;
    a dispenser member mounted on said reservoir; and
    a body configured to receive said reservoir, said body provided with a dispenser orifice and an opening through which said reservoir is inserted into the body, said reservoir displaceable in said body between a rest position and a dispensing position, said reservoir removable from said body;
    said reservoir comprises a first ID and said body comprises a second ID, said first and second IDs are uniquely associated with each other so that said reservoir is confirmed to be uniquely associated with said body by matching the first ID with the second ID and thereby prevent another reservoir from being accidentally associated with the body;
    the body is provided with a counter or indicator device that counts or indicates doses of fluid that have been dispensed or that remain to be dispensed from the reservoir.

9. The fluid dispenser device according to claim 8, wherein the first ID is identical to the second ID.

10. The device according to claim 1, wherein the ID means of the reservoir is identical to the ID means of the body.

* * * * *